United States Patent [19]

Itil et al.

[11] 4,045,562

[45] * Aug. 30, 1977

[54] LISURIDE AND PHYSIOLOGICALLY ACCEPTABLE SALTS THEREOF TO ACHIEVE PSYCHIC ENERGIZER EFFECTS

[75] Inventors: Turan M. Itil, Nyack, N.Y.; Werner Martin Herrmann, Berlin, Germany

[73] Assignee: Schering Aktiengesellschaft, Berlin & Bergkamen, Germany

[*] Notice: The portion of the term of this patent subsequent to May 4, 1993, has been disclaimed.

[21] Appl. No.: 688,559

[22] Filed: May 21, 1976

[30] Foreign Application Priority Data

May 22, 1975 Germany .............................. 2523026

[51] Int. Cl.² .................... A61K 31/48; A61K 31/475

[52] U.S. Cl. ...................................... 424/261; 424/262
[58] Field of Search ................................ 424/261, 262

[56] References Cited

U.S. PATENT DOCUMENTS 3,954,988  5/1976  Itil et al. ............................... 424/261

Primary Examiner—Stanley J. Friedman
Attorney, Agent, or Firm—Millen & White

[57] ABSTRACT

Lisuride and its acid addition salts are effective to achieve psychic energizer effects in patients having psychic disturbances who respond poorly to the effects thereof at lower dosages at higher dosages of from 300 to 1,000 μg.

6 Claims, No Drawings

LISURIDE AND PHYSIOLOGICALLY ACCEPTABLE SALTS THEREOF TO ACHIEVE PSYCHIC ENERGIZER EFFECTS

BACKGROUND OF THE INVENTION

This invention relates to the use of lisuride and the physiologically acceptable salts thereof to achieve psychic energizer effects.

It is known from Canadian Pat. No. 885,976 that lisuride hydrogen maleate is useful as a serotonin antagonist for the treatment of migraine, allergies, the dumping syndrome, and argentaffinoma. Heretofore, nothing has been reported regarding a psychotropic activity of lisuride hydrogen maleate.

For the most part, phenylethylamine derivatives, such as amphetamine and methamphetamine, have been used as psycho-pharmaceuticals with a psychic energizer effect. These agents have high toxicity. Furthermore, they exert a stimulating effect and a phase of exhaustion after their use. It has been reported that these compounds evoke psychotic conditions and that these symptoms are very similar to the symptoms of paranoic schizophrenia. Also, a tolerance with respect to their effectiveness develops. Also, the amphetamines exhibit great dependency and abuse potential.

In our prior application Ser. No. 526,303, filed Nov. 22, 1974, now U.S. Pat. No. 3,954,988, we claim a method for the treament of psychic disturbances comprising the administration of lisuride or a physiologically acceptable salt thereof in an amount effective to ameliorate the phychic disturbance. As disclosed therein, the usual daily dosage is 1-300 μg., preferably 1-40 μg., administered all at once or in divided dosages, with the usual oral unit of administration being 1-100 μg., preferably 1-20 μg.

It has now been found that, surprisingly, in patients relatively intractable to lisuride therapy at these early dosage ranges can be benefited at higher dosage ranges.

SUMMARY OF THE INVENTION

This invention relates to a method for the treatment of physchic disturbances manifested in
 a. a behaviorally disturbed and/or hyperkinetic child suffering from loss of concentration and memory and learning difficulties;
 b. an adolescent or adult with so-called neurasthenic symptomatology with at least one of the symptoms of loss of interest, loss of drive and activity, loss of concentration and learning ability; or
 c. a geriatric patient with loss of interest, loss of drive and activity, loss of energy and functional capacity, loss of concentration and learning ability combined with severe disturbance in mental function, which comprises administering to the affected patient a daily dosage from 300 to 1,000 μg of N-D-6-methyl-8-isoergolenyl-N,N'-diethylurea or a physiologically acceptable salt thereof effective to ameliorate the psychic disturbance.

DETAILED DISCUSSION

This invention is based upon the discovery that patients as described above who respond poorly to lisuride therapy at conventional dosages, i.e., at a daily dosage of 1-300 μg., surprisingly respond in a satisfactory manner to such therapy at a daily dosage in excess thereof, viz., from 300 to 1,000 μg., preferably from 300 to 600 μg.

Physiologically acceptable salts of lisuride are the acid addition salts of lisuride with inorganic and organic acids. Especially suitable for the formation of these salts are, for example, hydrochloric acid, methanesulfonic acid, glucoheptanoic acid, succinic acid, tartaric acid, maleic acid, etc. A preferred salt is the lisuride hydrogen maleate.

Lisuride [N-(D-6-methyl-8-isoergolenyl)-N',N'-diethylurea] hydrogen maleate is described, for example, in Belgian Pat. No. 703,487. Other physiologically acceptable salts can be prepared analogously. In the examples hereinafter, a molar equivalent of another acid can be subsituted for the hydrogen maleate.

Lisuride and the physiologically acceptable salts thereof are psychic energizers without simultaneously exhibiting the disadvantages (stimulating effect and development of dependency) of the phenylethylamine derivatives. There is a significant therapeutic effect in so-called neurasthenic symptomatology, mainly in the following symptoms: loss of interest, loss of drive and activity, loss of energy and functional capacity, loss of concentration and learning ability. They possess surprisingly high compatibility even at the large doses of this invention and there is no development of dependency, even after long-term administration at these large dosages.

The spectrum of psychic energizer activity, discovered with the aid of the quantitative Pharmaco-EEG, (T. M. Itil; Diseases of the Nervous System 8 (1972) 8) is novel and has not been found for another drug. The objective results are laid down in parameters of the EEG's analyzed by computer and the spectrum of effectiveness is characterized by a decrease of the delta and theta waves, and increase in the alpha and slow beta waves, as well as a decrease of the superimposed fast waves (up to 100/second). These phenomena affecting the physiology of the brain point to certain stimulating and simultaneously inhibiting effects exerted by lisuride. Accordingly, lisuride has a clinical spectrum of activity which can be called "Energizer Anxiolytic" (T. M. Itil et al., Int. J. Clin. Pharmacol. Ther. & Toxicol. 10[1974]143).

Lisuride and the physiologically acceptable salts thereof were tested in man in a placebo-controlled double blind experiment by quantitative Pharmaco-electroencephalography (CEEG) (T. M. Itil; Mod. Probl. Pharmacopsychiat., Vol. 8, Karger, Basel-New York [1974]). The effects and side effects were determined by various rating scales, e.g., for the neurological and psychosomatic symptomatology, by self-rating scales for sedation, anxiety and depression, as well as by physicians' interviews. Furthermore, human pharmacological investigations were conducted to determine compatibility at the high dosages of this invention.

Upon administration of lisuride and the physiologically acceptable salts thereof, the desired effect occurs already shortly after administration, viz., after about 2-3 hours. This is surprising, since in the prophylactic treatment of migraine with lisuride hydrogen maleate the therapeutic effect can be detected only after 3-4 weeks.

The invention relates to a method for the treatment of patients of any age suffering from disturbances of drive and interest and disturbances of mood, behavior, energy, and functional efficiency and which exhibit poor response to lisuride therapy at conventional dosages, i.e., daily dosages of 1-300 μg., usually 1-40 μg. Among these disturbances are phenomena such as adynamia, apathy, lack of energy, lack of drive, drop in efficiency, loss of interest and disturbances of the powers of concentration and memory. This can refer, for example, to psychophysiological disturbances, in persons of any age with thinking, concentration or behavioral disturbances or learning problems, but especially geriatric patients having problems such as weakness of memory and concentration and a general decrease in efficiency. Therefore, an application in geriatrics in particular is suitable due to the good compatibility of lisuride and its salts even at high dosages. The effect also relates to patients having a pathological appetitie or abnormal motoric (hyperkinetic and hypokinetic conditions), as well as certain forms of manic-depressive psychoses. Among these are psychic disturbances, such as, for example, depression and anxiety syndrome.

In medical practice, lisuride and the physiologically acceptable salts thereof can be administered subcutaneously, intramuscularly, but preferably orally.

The daily dosage is from 300 to 1,000 µg., preferably 300–600 µg. The whole dosage can be administered all at once or in several divided doses. For the higher dosages, a gradual initiation of the therapy is advantageous. Lisuride and the physiologically acceptable salts thereof are also suitable for a long-term treatment, since no psychic dependency is produced.

Drug preparations containing lisuride or a physiologically salt thereof are prepared in a manner known per se by processing lisuride or a physiologically acceptable salt thereof with the vehicles, diluents, flavor-ameliorating agents, etc., customary in galenic pharmacy.

Suitable for injections are oily solutions or suspensions, e.g. solutions or suspensions in sesame, castor and cottonseed oil.

To prepare intramuscular depot formations, lisuride or a physiologically acceptable salt thereof can be suspended or dissolved in a fatty oil according to conventional methods. Such depot forms contain about 500–2000 µg. of active agent per unit of administration so that the active compound is released over a time period of about 2–20 days.

Suitable forms for oral administration are tablets, capsules, dragees, pills, suspensions and solutions.

The amount of active agent per oral unit of administration is 100–500 µg.

Also suitable are oral timed-release forms obtained in the usual way, for example, by the addition by hydrogenated fats and processing with resinogenous substances or by microencapsulation.

Drops for oral administration can be produced by suspending the active agent in an oil with the addition of flavor-ameliorating agents and/or solubilizers, for example, 100–200 µg. of lisuride or an acid addition salt thereof in a daily dosage of 3 × 10 drops.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

A homogeneous mixture is produced from 0.100 mg. lisuride hydrogen maleate (micronized) with
0.200 mg. tartaric acid
0.050 mg. disodium edetate
59.250 mg. lactose
20.000 mg. microcellulose and
0.400 mg. magnesium stearate 80.000 mg.

Without previous granulation, tablets are compressed from this mixture with a breaking notch and weighing 80 mg.

EXAMPLE 2

Analogously to Example 1, tablets having a final weight of 80 mg. are compressed from 0.200 mg. lisuride hydrogen maleate with
0.200 mg. tartaric acid
0.050 mg. disodium edetate
59.150 mg. lactose
20.000 mg. microcellulose and
0.400 mg. magnesium stearate 80.000 mg.

EXAMPLE 3

Analogously to Example 1, tablets having a final weight of 80 mg. are compressed from 0.500 mg. lisuride hydrogen maleate with
0.200 mg. tartaric acid
0.050 mg. disodium edetate
58.850 mg. lactose
20.000 mg. microcellulose and
0.400 mg. magnesium stearate 80.000 mg.

EXAMPLE 4

Respectively 0.200 mg. of lisuride hydrogen maleate (micronized, particle size about 20 µ.) is mixed homogeneously with 150 mg. of lactose and filled into hard gelatin capsules (5 × 15 mm.).

EXAMPLE A

Effect of high dosages of lisuride on geriatric patients with psychosomatic complaints and mental disturbances.

In an open pilot trial without any control drugs, the effect of lisuride has been studied in a group of 8 male and 6 female patients. The age range was 45–75 years. The diagnosis was based on rating scales and performance tests. Lisuride was given in a dosage of 500 µg daily for a period of 8 weeks. The results are based on the clinical rating scales and the performance tests. Lisuride acted as psychostimulant and neotropic agent in 6 out of the 8 male and in 5 out of the 6 female patients. The improved symptoms were memory and concentration, improvement in neuroticism, psychosomatic complaints and improvement in motoric and mental performance. There was no change in the laboratory control test from pre- to post-treatment and despite some nausea at the beginning of the treatment no remarkable side effects were observed.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for the treatment of psychic disturbances manifested by
   a. behaviorally disturbed and/or hyperkinetic children suffering from loss of concentration and memory and learning difficulties,
   b. adolescents and adults with so-called neurasthenic symptomatology with at least one of the following symptoms:
   loss of interest, loss of drive and activity, loss of energy and functional capacity, loss of concentration and learning ability, and
   c. geriatric patients with loss of interest, loss of drive and activity, loss of energy and functional capacity, loss of concentration and learning ability combined with severe disturbances in mental function,
   which comprises administering to the affected patient a daily dosage of from 300 μg. to 1,000 μg. of N-D-6-methyl-8-isoergolenyl-N',N'-diethylurea or a physiologically acceptable acid addition salt thereof effective to ameliorate the psychic disturbance.

2. A method according to claim 1 wherein the administration is oral.

3. A method according to claim 1 wherein the affected patient is a geriatric.

4. A method according to claim 1 wherein the daily dosage is from 300 to 600 μg.

5. A method according to claim 1 wherein the administration is oral is divided dosages and the dosage per administration is 100–500 μg.

6. A method according to claim 5 wherein the affected patient is a geriatric.

* * * * *